United States Patent [19]

Shimizu et al.

[11] Patent Number: 4,967,009
[45] Date of Patent: Oct. 30, 1990

[54] METHOD FOR OXIDIZING UNSATURATED AROMATIC COMPOUNDS

[75] Inventors: Isoo Shimizu; Yasuo Matsumura, both of Yokohama; Kouichi Iwamoto, Kawasaki, all of Japan

[73] Assignee: Nippon Petrochemicals Co., Ltd., Tokyo, Japan

[21] Appl. No.: 377,183

[22] Filed: Jul. 7, 1989

[30] Foreign Application Priority Data

Jul. 8, 1988 [JP] Japan .................................. 63-170577
Jul. 8, 1988 [JP] Japan .................................. 63-170578
Jul. 8, 1988 [JP] Japan .................................. 63-170579

[51] Int. Cl.$^5$ ............................................ C07C 00/00
[52] U.S. Cl. ................................... 568/309; 568/306; 568/322; 568/426
[58] Field of Search ............... 568/306, 309, 310, 322, 568/426

[56] References Cited

FOREIGN PATENT DOCUMENTS 1450200 8/1966 France .................................. 562/443
1119612 7/1968 United Kingdom ................. 568/800

OTHER PUBLICATIONS

Kinneary et al., J.A.C.S., vol. 110, pp. 6124–6129, (1988).
Collins et al., J. Chem. Soc. Chem. Commun., pp. 803–804, (1987).
Koola et al., J. Org. Chem., vol. 52, pp. 4545–4553, (1987).
Tai et al., J.A.C.S., vol. 108, pp. 5006–5008, (1986).
G. A. Stein et al., *J. Am. Chem. Soc.*, 77:700–703, (1955).
V. M. L. Hallensleben, *Die Angewandte Makromolekulare Chemie*, 27:223–227, (1972).
Y. Yamada et al., *Die Makromolekulare Chemie*, 152:153–162, (1972).

*Primary Examiner*—James H. Reamer
*Attorney, Agent, or Firm*—Scully, Scott, Murphy & Presser

[57] ABSTRACT

This invention relates to a method for manufacturing aromatic compounds having the following formula (II) comprising the step of reacting an unsaturated aromatic compound having the following formula (I) with an aryl compound containing an iodosyl group or the salt thereof within a temperature range of from −50° to 200° C.:

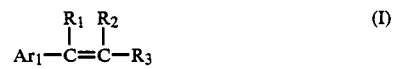

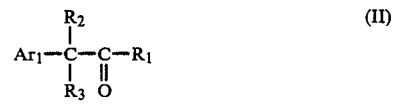

8 Claims, No Drawings

METHOD FOR OXIDIZING UNSATURATED AROMATIC COMPOUNDS

BACKGROUND OF THE INVENTION (1) Field of the Invention

This invention relates to a novel method for oxidizing unsaturated aromatic compounds.

There are many oxidized products useful for an intermediate material for various agricultural chemicals, pharmaceuticals and the like which are obtained by oxidizing unsaturated aromatic compounds.

For example, an arylacetone such as 4-hydroxy-3-methoxyphenylacetone, 3, 4-dimethoxyphenylacetone, 3, 4-dihydroxyphenylacetone or the like is a compound used as an intermediate for manufacturing L-α-methyldopa which is employed as an antihypertensive agent. Furthermore, 2-(4-isobutylphenyl) propionaldehyde is utilized as an intermediate for 2-(4-isobutylphenyl) propionic acid (trade name: ibuprofen) having antipholog-istic, antipyretic and lenitive actions, and (4-isobutylphenyl)acetaldehyde is an intermediate of (4-isobutylphenyl) acetic acid (trade name: ibufenac) having the same pharmacological effects as those of the former compound.

(2) Description of the Prior Art

Among these useful compounds, arylacetones exhibiting high utility and for which various manufacturing methods have heretofore been proposed will be described hereinbelow as a specific example thereof. There have been proposed the following typical methods as ones for manufacturing arylacetones.

(1) British Patent No. 1,119,612 discloses a method in which a peroxide such as peracetic acid or the like is allowed to act on 1-(3, 4-dimethoxyphenyl)propylene, and the resulting diol type product is treated with an acid material such as zinc chloride to obtain 3, 4-dimethoxyphenylacetone.

(2) French Patent No. 1,450,200 discloses a method in which 3, 4-dimethoxybenzaldehyde is reacted with α-chloropropionic acid ester in the presence of a strong alkali, and the reaction product is then treated with a strong acid to obtain 3, 4-dimethoxyphenylacetone.

(3) Journal of American Chemical Society (JACS), 77, 700 (1955) describes a method in which 3, 4-dimethoxyphenylacetonitrile is reacted with sodium ethoxide in a solvent such as ethyl acetate thereby to transform the former into an acetyl-member, and then the acetyl-member thus obtained is hydrolyzed to obtain 3, 4-dimethoxyphenylacetone.

The above described method 1) involves such problems in that an yield is low in the process of the treatment by the use of an acid material and that since a peroxide used is explosive, special care is required for handling the same.

Furthermore, in the method 2), it is difficult to state that the raw materials 3, 4-dimethoxybenzaldehyde and α-chloropropionic acid ester are easily available.

The method (3) involves such problems in that it is necessary to carry out the reaction in a system from which water has been strictly removed in case of using sodium ethoxide therein for the sake of preventing hydrolysis of such sodium ethoxide, that a yield is low in the hydrolysis step, and that the number of steps in the method becomes excessive as a whole if steps required for manufacturing a raw material 3, 4-dimethoxyphenylacetonitrile itself from an easily available chemical material are taken into consideration.

As discussed above, it must be said that all the manufacturing methods (1), (2) and (3) have not yet been satisfactory from industrial point of view.

OBJECT OF THE INVENTION

An object of the present invention is to manufacture oxidized products of unsaturated aromatic compounds useful for intermediate materials for various agricultural chemicals, pharmaceuticals and the like from easily available and in inexpensive raw materials in a high yield, besides to provide also a method for manufacturing, for example, arylacetone from easily available raw materials in a high yield.

SUMMARY OF THE INVENTION

The present invention relates to a method for manufacturing oxidized products of unsaturated aromatic compounds useful for intermediate materials for various agricultural chemicals, pharmaceuticals and the like from easily available and inexpensive raw materials in a high yield.

In other words, the present invention relates to a novel method for oxidizing unsaturated aromatic compounds characterized by reacting an unsaturated aromatic compound with an aryl compound having an iodosyl group or the salt thereof.

DETAILED DESCRIPTION OF THE INVENTION

The method of the present invention is carried out by using an easily available unsaturated aromatic compound as a raw material, and reacting the same with an aryl compound having an iodosyl group or the salt thereof.

The raw material of the present invention is an unsaturated aromatic compound having the following general formula (I):

wherein $Ar_1$ is an aryl group which is a substituent obtained by drawing one hydrogen atom from an aromatic ring of an aromatic hydrocarbon such as phenyl, naphthyl, biphenylyl or the like group and said aryl group may be substituted by one to three substituents selected from the group consisting of halogen atoms such as chlorine, fluorine, bromine, iodine and the like, nitro group, amino group, a lower alkyl group such as methyl, ethyl or the like group, and a lower alkoxy group such as methoxy, ethoxy or the like group; and $R_1$, $R_2$ and $R_3$ are hydrogen atom; lower alkyl groups each having 1 to 4 carbon atoms such as methyl, ethyl, propyl, isopropyl, butyl, isobutyl and the like; aryl groups such as phenyl, naphthyl, bisphenyl and the like group which may be substituted by one to three substituents selected from the group consisting of halogen atoms such as chlorine, fluorine, bromine, iodine and the like, nitro group, amino group, and lower alkoxy groups such as methoxy, ethoxy and the like groups; further, $R_1$, $R_2$ or $R_3$ may form a ring structure with $Ar_1$; and $R_1$, $R_2$ and $R_3$ may also be identical with each other.

Specific examples of the unsaturated aromatic compounds having the above described formula (I) include aryl ethylenes such as styrene, 4-methylstyrene, 3-methylstyrene, 2-methylstyrene, 4-ethylstyrene, 4-isopropylstyrene, 4-isobutylstyrene, 4-phenylstyrene, 4-chlorostyrene, 2-chlorostyrene, 3-chlorostryene, 4-bromostyrene, 4-nitrostyrene, 4-methoxystyrene, 3-benzoylstyrene, 3-benzylstyrene, 6-methoxy-2-naphthylethylene and the like; 1-aryl propylenes such as 1-phenylpropylene, 1-(chlorophenyl)propylene, 1-(fluorophenyl)propylene, 1-(bromophenyl)propylene, 1-(nitrophenyl)propylene, 1-(dimethylaminophenyl)propylene, 1-(methylphenyl)propylene, 1-(dimethylphenyl)propylene, 1-(ethylphenyl)propylene, 1-(4-isobutylphenyl)propylene, 1-(3-trifluoromethylphenyl)propylene, 1-(methoxyphenyl)propylene, 1-(3, 4-dimethoxyphenyl)propylene, 1-(3-benzoylphenyl)propylene, 1-(6-methoxy-2-naphthyl)propylene, 1-biphenylylpropylene and the like; 2-aryl propylenes such as 2-phenylpropylene, 2-(chlorophenyl)propylene, 2-(fluorophenyl)propylene, 2-(4-bromophenyl)propylene, 2-(nitrophenyl)propylene, 2-(dimethylaminophenyl)propylene, 2-(methylphenyl)propylene, 2-(ethylphenyl)propylene, 2-(3-trifluoromethylphenyl)propylene, 2-(methoxyphenyl)propylene, 2-(3, 4-dimethoxyphenyl)propylene, 2-(ethoxyphenyl)propylene, 2-(3-phenoxyphenyl)propylene, 2-naphthylpropylene, 2-(6-methoxy-2-naphthyl)propylene, 2-benzoylphenylpropylene, 2-biphenylylpropylene and the like; 1-aryl-1-butenes such as 1-phenyl-1-butene, 1-(3-bromophenyl)-1-butene, 1-(4-chlorophenyl)-1-butene and the like; 2-aryl-1-butenes such as 2-phenyl-1-butene, 2-(4-methylphenyl)-1-butene and the like; 2-aryl-2-butenes such as 2-phenyl-2-butene, 2-(2-methylphenyl)-2-butene, 2-(4-methylphenyl)-2-butene, 2-(4-isobutylphenyl)-2-butene and the like; 1-aryl-2-methylpropylenes such as 1-phenyl-2-methylpropylene, 1-(4-methylphenyl)-2-methylpropylene, 1-(4-chlorophenyl)-2-methylpropylene, 1-(3-bromophenyl)-2-methylpropylene, 1-(4-bromophenyl)-2-methylpropylene and the like; aryl pentenes; aryl hexenes; diarylethylenes such as 1, 1-diphenylethylene, 1, 1-bis(methylphenyl)ethylene, 1, 1-bis(chlorophenyl)ethylene, 1-phenyl-1-(4-methylphenyl)ethylene, 1-phenyl-1-(4-fluorophenyl)ethylene, 1-phenyl-1-(4-chlorophenyl)ethylene, 1-phenyl-1-(4-bromophenyl)ethylene, 1, 2-diphenylethylene and the like; or such compounds obtained by forming a ring structure from $R_1$, $R_2$ or $R_3$ in the aforesaid formula (I) with $Ar_1$ such as 1, 2-dihydronaphthalene, indene, and 1, 2-dihydroanthracene.

According to the method of the present invention, the above-mentioned unsaturated aromatic compounds are oxidized to obtain the corresponding oxides. These products thus oxidized have the following general formula (II):

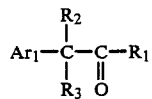
(II)

wherein $Ar_1$, $R_1$, $R_2$ and $R_3$ have the same meanings as defined in the above formula (I), respectively.

As is apparent from the comparison of the aforesaid formula (I) with the formula (II), according to the method of the present invention, the compounds which are products oxidized having the formula (II) are obtained seemingly in such a manner that the substituent $Ar_1$ in the formula (I) transfers to the carbon atom with which are combined $R_2$ and $R_3$, whilst a carbonyl group is introduced into the place where the $Ar_1$ was left.

Specific examples of the oxidized products manufactured in accordance with the method of the present invention are the compounds oxidized corresponding to said unsaturated aromatic compounds and which include, for example, aryl acetaldehydes, 2-aryl-propionaldehydes, aryl acetones, 2-aryl butylaldehydes, 1-aryl-2-butanones, 3-aryl-2-butanones, 2-aryl-2-methylpropionaldehydes, and diaryl ethanones which correspond to aryl ethylenes, 1-aryl propylenes, 2-aryl propylenes, 1-aryl-1-butenes, 2-aryl-1-butenes, 2-aryl-2-butenes, 1-aryl-2-methylpropylenes, and 1, 1-diaryl ethylenes, respectively.

In the present invention, an aryl compound having at least one iodosyl group or the salt thereof is reacted with an unsaturated aromatic compound having said formula (I).

The aryl compound having an iodosyl group is represented by the following general formula (III):

$$Ar_2-I=O \qquad (III)$$

wherein aryl group $Ar_2$ is an aromatic hydrocarbon residue such as phenyl, naphthyl, biphenylyl and the like group, and these aryl groups may be substituted by one or more of lower alkyl groups such as methyl, ethyl, propyl and the like groups, lower alkoxy groups such as methoxy, ethoxy and the like groups, nitro group, carboxyl group and the like.

A specific example of the aforesaid aryl compound having an iodosyl group includes iodosylbenzene, o-, m- or p-substituted iodosyltoluene, 2-iodosyl m-xylene, 2-iodosyl p-xylene, o-, m- or p-substituted iodosylanisole, o-iodosylphenetole, o-iodosylphenoxybenzene, 4-iodosylbiphenyl, o-, m- or p-substituted nitroiodosylbenzene, p-iodosylbenzoic acid or the like.

These aryl compounds having iodosyl groups may be used either without any modification or in the form of salts.

The salts of an aryl compound containing an iodosyl group as described above may be salts of inorganic or organic acids. Examples of the organic acid include carboxylic acids, for example, lower fatty acids such as acetic acid, propionic acid, butyric acid and the like, halogenated lower fatty acids such as chloroacetic acid, dichloroacetic acid, bromoacetic acid, trifluoroacetic acid and the like, aromatic carboxylic acids such as benzoic acid, methylbenzoic acid and the like, halogenated aromatic carboxylic acids such as bromobenzoic acid, chlorobenzoic acid and the like, nitrated aromatic carboxylic acids such as nitrobenzoic acid and the like, or the like carboxylic acids. Other than those mentioned above, salts of acids such as nitric acid, sulfonic acid and the like are used, and preferably salts of carboxylic acids, nitric acid or sulfonic acid are employed. A salt of the aryl compound having an iodosyl group has the following general formula (IV):

$$Ar_2-I(X)_2 \qquad (IV)$$

wherein $Ar_2$ is an aromatic hydrocarbon residue such as phenyl, naphthyl, biphenylyl and the like groups, and these aryl groups may be substituted by one or more of lower alkyl groups such as methyl, ethyl, propyl and the like groups, lower alkoxy groups such as methoxy, ethoxy and the like groups, nitro group, carboxyl group and the like; and ion X is an acid residue.

Specific examples of said salt of aryl compound include acetates such as iodosylbenzene diacetate, o-, m- or p-substituted iodosyltoluene diacetate, 2-iodosyl-m-xylene diacetate, 2-iodosyl-p-xylene diacetate, o-, m- or p-substituted iodosylchlorobenzene diacetate, o-, m- or p-substituted iodosylnitrobenzene diacetate, 4-iodosylethoxybenzene diacetate, 4-iodosylcyanobenzene diacetate, iodosylbiphenyl diacetate, α-iodosylnaphthalene diacetate and the like; haloacetates such as iodosylbenzene di(chloroactate), iodosylbenzene di(dichloroactate), iodosylbenzene di(trichloroactate), iodosylbenzene di(bromoactate), iodosylbenzene di(trifluoroactate) and the like; benzoates such as iodosylbenzene dibenzoate, 2-iodosyltoluene dibenzoate, 2-iodosylchlorobenzene dibenzoate, 2-iodosylnitrobenzene dibenzoate, iodosylmesitylene dibenzoate and the like; substituted benzoates such as iodosylbenzene di(4-chlorobenzoate), iodosylbenzene di(4-bromobenzoate), iodosylbenzene di(2, 4-dinitrobenzoate), iodosylbenzene di(4-methoxybenzoate), iodosylbenzene di(4-methylbenzoate) and the like; besides iodosylbenzene di(p-toluenesulfonate), iodosylbenzene dinitrate, 2-iodosylnitrobenzene dinitrate, iodosylbenzene dipropionate, iodosylbenzene dihexanoate and the like.

Furthermore, the compounds each having an iodosyl group or the salts thereof according to the present invention may be high polymeric organic substances. More specifically, they may be a high polymeric organic substance to which has been added at least one compound containing an iodosyl group or the salt thereof. In a way, these substances are in such a form wherein an aryl group in the aryl compound having an iodosyl group which is represented by the aforesaid formula or the salts thereof is linked with the backbone chain of a high polymeric organic substance.

A specific aryl compound containing the aryl group with which may be linked a high polymeric organic backbone chain means a polymer or copolymer of styrene or the derivative monomer thereof. In these organic high-molecular weight compounds, an iodosyl group is introduced into the compounds by post-treating the polymer or copolymer of styrene or the derivative thereof, and then the iodosyl group may be transformed into a salt. Specifically, a method for introducing an iodosyl group by means of the after-treatment can be effected in accordance with a method described, for example, in Angew. Makromol. Chem., 27 (431), 223 (1972). Moreover, a method for converting the iodosyl group introduced into a salt can be specifically effected in accordance with a method described, for example, in Die Makromolekulare Chemie, 153–162 (1972).

It is required to use at least one equivalent of an aryl compound having an iodosyl group or the salts thereof with respect to a raw material unsaturated aromatic compound, and in general about one equivalent is sufficient for such unsaturated aromatic compound. Since there is no upper limit of an amount of the aryl compound to be used, even if the amount exceeds one equivalent, no obstacle is observed. However, the use of an excessive amount of such aryl compound is merely uneconomical, so that it is not desirable. On the other hand, when an amount of the aryl compound used is less than one equivalent, a raw material unsaturated aromatic compound remains unreacted in a ratio corresponding to such insufficient amount of the aryl compound so that it is undesirable.

After the reaction of the present invention, an aryl compound having an iodosyl group or the salts thereof become aryl iodides which can be easily recovered by distillation or filtration from the reaction products.

In the present invention, a catalyst may be used for the sake of accelerating the reaction, if necessary. As a reaction catalyst, a salt of transition metals such as cobalt, manganese, copper, iron and the like is used, and cobalt is preferably used as such a transition metal. A transition metal having any oxidation number can be used in the present invention without any trouble, so far as the oxidation number of the transition metal is not zero. As such a salt, there are illustrated salts of an organic acid such as acetic acid, butyric acid, naphthenic acid or the like; salts of an inorganic acid such as nitric acid, hydrochloric acid or the like; and complex salts such as acetylacetonato, triflate, octanoate and the like.

Specific examples of such catalyst as described above include cobalt, manganese, copper, or iron acetates, nitrates, naphthenates; or complex salts such as acetylacetonato, triflate, octanoate and the like.

An amount of such catalyst to be used is suitable within a range of, for example, 0.01–20% by weight, and preferably 0.05–10% by weight with respect to a raw material unsaturated aromatic compound. In the case where an amount of the catalyst used is less than the lower limit of such range, the reaction does not proceed sufficiently, whilst even if an amount of the catalyst used is allowed to exceed the upper limit of said range, it does scarcely contribute to elevation of the rate of reaction, and the situation becomes rather worse because recovery of the catalyst comes to take much time so that it is not desirable.

Furthermore, an acid may be allowed to exist in order to promote the reaction. Specifically, an acid such as hydrochloric acid, sulfuric acid, phosphoric acid, sulfonic acid or the like is used.

A reaction temperature ranges from −50° to 200° C., and preferably from 0° to 100° C. In case of a temperature of less than −50° C., since the temperature is too low, the reaction does not proceed, or a raw material unsaturated aromatic compound solidifies, so that it is undesirable. On the other hand, when the temperature exceeds 200° C., there are a case where an aryl compound having an iodosyl group or the salts thereof are decomposed, and a case where by-products are produced as a result of polymerization and the like of a reaction raw material unsaturated aromatic compound. Thus, selectivity of the product to be manufactured decreases remarkably so that temperatures out of said range are undesirable. While a reaction time depends on a reaction condition such as a reaction temperature and the like, it is within a range of from 10 minutes to 10 hours, in usual.

Since the reaction of the present invention is never affected by a pressure in the reaction system at the time of such reaction, it may be suitably selected, but usually normal pressures are satisfactory.

In the method of the present invention, although it is not necessarily required to use a solvent for the reaction, an inert solvent with respect to the reaction may be used in order to improve contact efficiency of the aryl compound having an iodosyl group or the salts thereof with an unsaturated aromatic compound. As such solvent as described above, for example, water, acetone, alcohols such as methanol, t-butyl alcohol and the like, glacial acetic acid, acetonitrile, isooctane, benzene, chloroform and the like are used, and they may be used either alone or in the form of a mixed solvent of them.

The method of the present invention may be carried out, for example, as follows.

A reaction vessel is charged with an unsaturated aromatic compound, an aryl compound having an iodosyl group or the salts thereof and a solvent, and the reaction is allowed to proceed under a prescribed condition, and in this case any order is not particularly determined for the addition of these components.

After the reaction, a reaction mixture is extracted with an organic solvent such as benzene, ethyl acetate, chloroform or the like in accordance with a conventional procedure, and then a high-purity oxidized product of the unsaturated aromatic compound is easily obtained by either usual distillation or recrystallization of the resulting reaction mixture.

As described above, when an unsaturated aromatic compound, the aromatic ring of which may have a substituent, is reacted with an aryl compound having an iodosyl group or the salts thereof in accordance with the present invention, an oxidized product of the unsaturated aromatic compound which is useful for an intermediate raw material of various agricultural chemicals, pharmaceuticals and the like can be manufactured in a high yield.

EXAMPLES

The present invention will be described further in conjunction with the following examples, but it is to be understood that the invention is not limited by only these examples in which the percentages are by weight otherwise specified.

EXAMPLE 1

A reaction vessel was charged with 2-phenylpropylene (3 mmol) as a raw material unsaturated aromatic compound, iodosylbenzene diacetate (3 mmol) as a salt of an iodosyl compound and 30 ml of 60% aqueous acetic acid as a solvent, and the reaction was carried out under such condition of 25° C. reaction temperature and 2 hour reaction time in nitrogen atmosphere.

After completing the reaction, the reaction solution was poured to water, and then an oily matter was extracted with ether. After removing the ether by distillation, a degree of reaction of the raw material 2-phenylpropylene and an yield of phenylacetone being the product to be produced were 30% and 26%, respectively, as a result of a gas chromatograph analysis, and in this case iodobenzene being a by-product in the reaction was also observed.

Furthermore, it was confirmed that the objective product phenylacetone obtained was the same with a standard sample as a result of NMR, IR and MASS analyses.

EXAMPLES 2–8

Each reaction was carried out by using the starting material and the like enumerated in the following Table in accordance with the above described manner in Example 1, and the results are shown in the same Table.

EXAMPLE 9

A reaction was effected by employing cobalt acetate as the catalyst in glacial acetic acid in accordance with the reaction of Example 1. After the reaction, the resulting product was post-treated in accordance with the manner in Example 1. As a result of the same analysis, a degree of reaction and an yield were 100% and 44%, respectively.

EXAMPLES 10–31

Each reaction was carried out by using the starting material and the like enumerated in the following Table in accordance with the above described manner in Example 9, and the results are shown in the same Table.

EXAMPLES 32–40

Each reaction was carried out by using the catalyst or the reaction solvent enumerated in the following Table in accordance with the above described manner in Example 9, and the results are shown in the same Table.

EXAMPLE 41

A reaction vessel was charged with 2-phenylpropylene (3 mmol) as an unsaturated aromatic compound (raw material), modified polystyrene beads 15% of which are occupied by a unit having an iodosyl group (2.85 g), cobalt acetate (0.05 mmol) as a catalyst and 100 ml of glacial acetic acid as a solvent, and the reaction was carried out under such condition of 25° C. reaction temperature and 2 hour reaction time in nitrogen atmosphere.

After completing the reaction, the modified beads and the catalyst were filtered off, and then the filtrate was extracted with ether. After removing the ether by distillation, a degree of reaction of the raw material 2-phenylpropylene and an yield of phenylacetone being the product to be produced were 55% and 15%, respectively, as a result of a gas chromatograph analysis.

Furthermore, it was confirmed that the objective product phenylacetone obtained was the same with a standard sample as a result of NMR, IR and MASS analyses.

EXAMPLE 42

A reaction vessel was charged with 2-(3, 4-dimethoxyphenyl)propylene (3 mmol) as an unsaturated aromatic compound (a raw material), modified polystyrene beads 25% of which are occupied by a unit in which acetic acid has been added to an iodosyl group (1.6 g) as a high-molecular weight aromatic compound, cobalt nitrate (0.05 mmol) as a catalyst and 100 ml of 60% aqueous acetic acid as a solvent, and the reaction was carried out under such condition of 25° C. reaction temperature and 2 hour reaction time in nitrogen atmosphere.

As a result of the post-treatment in accordance with the above described manner in Example 41, the degree of reaction and the yield were 43% and 12%, respectively.

TABLE

| Ex. No. | I Com. | Cat. | R. Sol. | R. Tem. °C. | Time Hr | U.A. Com. | O.P. | Deg. of R. % | yield % |
|---|---|---|---|---|---|---|---|---|---|
| 1 | I BE diAE | No | 60% A AD | 25 | 10 | 2-PH PL | PH AN | 30 | 26 |
| 2 | " | " | 30% A AD | " | " | 2-(3,4-di MY PH)PL | 3,4-di MY PH AN | 35 | 31 |
| 3 | 4-I TL | " | 60% A AD | " | " | 2-(3-NR PH) | 3-NR PH | 24 | 15 |

TABLE-continued

| Ex. No. | I Com. | Cat. | R. Sol. | R. Tem. °C | Time Hr | U.A. Com. | O.P. | Deg. of R. % | yield % |
|---|---|---|---|---|---|---|---|---|---|
|  |  |  |  |  |  | PL | AN |  |  |
| 4 | I TL diBT | " | G AD | " | " | 2-(2-NL)PL | 2-NL AN | 21 | 7 |
| 5 | I BE di (CL AE) | " | " | 40 | " | 2-(4-ML PH) PL | 4-ML PH AN | 40 | 12 |
| 6 | 4-NR I BE | " | " | 25 | " | 2-PH PL | PH AN | 10 | 3 |
| 7 | 4-I TL | " | " | " | " | " | " | 30 | 8 |
| 8 | I BE diAE | " | AR | " | " | " | " | 10 | 3 |
| 9 | " | Co-AE | G AD | " | 2 | " | " | 100 | 44 |
| 10 | 4-I TL | " | " | " | " | " | " | 90 | 40 |
| 11 | I BE di (CL AE) | " | " | " | " | " | " | 79 | 32 |
| 12 | I BE diAE | " | " | " | " | 2-(4-MY PH) PL | 4-MY PH AN | 93 | 38 |
| 13 | " | " | " | " | " | 2-(3-CL-4- EY PH)PL | 3-CL-4- EY PH AN | 85 | 41 |
| 14 | " | " | " | " | " | 2-(4-isoBT PH)PL | 4-isoBT PH AN | 98 | 45 |
| 15 | " | " | " | " | " | 2-(3-NR PH) PL | 3-NR PH AN | 61 | 25 |
| 16 | " | " | " | " | " | 2-(4-N,N-di ML AM PH)PL | 4-N,N-diML AM PH AN | 90 | 40 |
| 17 | " | " | " | " | " | 2-(2-NL)PL | 2-NL AN | 66 | 29 |
| 18 | " | " | 60% A AD | " | " | ST | PH AA | 94 | 55 |
| 19 | " | " | " | " | " | 4-ML ST | 4-ML PH AA | 98 | 61 |
| 20 | " | " | " | " | " | 4-CL ST | 4-CL PH AA | 90 | 47 |
| 21 | " | " | " | " | " | 1-PH PL | 2-PH PN AL | 75 | 49 |
| 22 | " | " | " | " | " | 1-(4-isoBT PH)PL | 2-(4-isoBT PH)PN AL | 78 | 48 |
| 23 | " | " | " | " | " | 1-(3-BL PH) PL | 2-(3-BL PH) PN AL | 42 | 25 |
| 24 | " | " | " | " | " | 1-(6-MY-2- NL)PL | 2-(6-MY-2- NL)PN AL | 80 | 54 |
| 25 | " | " | " | " | " | 2-PH-1-BN | 1-PH-2-BO | 88 | 68 |
| 26 | " | " | " | " | " | 2-PH-2-BN | 3-PH-2-BO | 93 | 81 |
| 27 | I BE diAE | Co-AE | 60% A AD | 25 | 2 | 2-(4-isoBT PH)-2-BN | 3-(4-isoBT PH)-2-BO | 96 | 84 |
| 28 | " | " | " | " | " | 1-PH-2-ML- PL | 2-PH-2ML PN AL | 85 | 25 |
| 29 | " | " | " | " | " | 1-(4-CL PH)- 2-ML PL | 2-(4-isoBT PH)-2-ML PN AL | 80 | 16 |
| 30 | " | " | " | " | " | 1,1-diPH EL | BZ MK | 92 | 52 |
| 31 | " | " | " | " | " | 1,2-diHN | 1-FI | 99 | 12 |
| 32 | " | " | " | " | " | 2-PH PL | PH AN | 99 | 90 |
| 33 | " | " | " | 100 | " | " | " | 100 | 78 |
| 34 | " | " | MT | 80 | " | " | " | 85 | 48 |
| 35 | " | Co-NE | AR | 25 | " | " | " | 50 | 16 |
| 36 | " | " | 60% A AD | " | " | 2-(3,4-diMY PH)PL | 3,4-diMY PH AN | 98 | 90 |
| 37 | " | " | Water | " | " | 2-(3,4-diMY PH)PL | 3,4-diMY PH AN | 99 | 85 |
| 38 | " | Mn-TF | G AD | " | " | 2-PH PL | PH AN | 80 | 32 |
| 39 | " | Cu-NE | " | 25 | " | " | " | 75 | 26 |
| 40 | " | Fe-TF | " | " | " | " | " | 60 | 18 |

Abbreviations used in the Table are as follows.
R. = reaction, Cat. = catalyst, Com. = compound, Sol. = solvent, Tem. = temperature, U.A. = unsaturated aromatic, O.P. = oxydized product, Deg. = degree, A = aqueous, AA = acetaldehyde, AD = acetic acid, AE = acetate, AL = aldehyde, AM = amino, AN = acetone, AR = acetonitrile, BE = benzene, BL = benzoyl, BN = butene, BO = butanone, BT = benzoate, BU = butyl, BZ = benzyl, CL = chloro, EL = ethyl, EY = ethoxy, FI = formylindane, G = glacial, HN = hydronaphthalene, I = iodosyl, MK = methyl ketone, ML = methyl, MT = methanol, MY = methoxy, NE = nitrate, NL = naphthyl, NR = nitro, PH = phenyl, PL = propylene, PN = propion, ST = styrene, TF = triflate, TL = toluene.

What is claimed is:

1. A method for manufacturing aromatic compounds having the following formula (II) comprising the step of reacting an unsaturated aromatic compound having the following formula (I) with an aryl compound having at least one iodosyl group or a salt thereof within a range of a reaction temperature of from −50° to 200° C.:

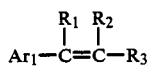

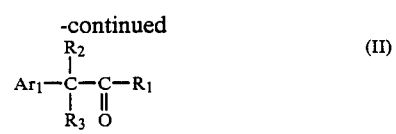

wherein $Ar_1$ is an aryl or substituted aryl group, each of $R_1$, $R_2$ and $R_3$ is hydrogen atom, a lower alkyl group having 1-4 carbon atoms or an aryl or substituted aryl group, and $R_1$, $R_2$ and $R_3$ may be the same or different groups, respectively.

2. The method for manufacturing aromatic compounds as claimed in claim 1 wherein the aryl group $Ar_1$ in said unsaturated aromatic compound is an aromatic hydrocarbon residue in which 1-3 hydrogen atoms of the aromatic ring thereof are substituted by a substituent or substituents selected from the group consisting of hydrogen atom, halogen atom, nitro group, amino group, lower alkyl group and lower alkoxy group.

3. The method for manufacturing aromatic compounds as claimed in claim 2 wherein said aromatic hydrocarbon residue is a phenyl group.

4. The method for manufacturing aromatic compounds as claimed in claim 1 wherein said reaction is conducted in the presence of a reaction catalyst, wherein said reaction catalyst is a salt of a transition metal selected from the group consisting of cobalt, manganese, copper and iron.

5. The method for manufacturing aromatic compounds as claimed in claim 1 wherein said aryl compound having an iodosyl group or the salts thereof have either the following formula (III) or formula (IV), respectively;

$$Ar_2-I=O \qquad (III)$$

$$Ar_2-I(X)_2 \qquad (IV)$$

in the above formulae, $Ar_2$ is aryl group, and ion X is acid residue.

6. The method for manufacturing aromatic compounds as claimed in claim 5 wherein said aryl compound having an iodosyl group or the salts thereof are iodosyl benzene or iodosyl benzene diacetate.

7. The method for manufacturing aromatic compounds as claimed in claim 1, wherein said aryl compounds having an iodosyl group or the salts thereof are polymeric aromatic compounds.

8. A method for manufacturing aromatic compounds as claimed in claim 5 wherein said ion X is carboxylic acid ion, nitric acid ion or sulfonic acid ion.

* * * * *